(12) United States Patent
Cimino

(10) Patent No.: US 6,368,299 B1
(45) Date of Patent: Apr. 9, 2002

(54) ULTRASONIC PROBE AND METHOD FOR IMPROVED FRAGMENTATION

(76) Inventor: William W. Cimino, 578 W. Sagebrush Ct., Louisville, CO (US) 80027

(*) Notice: Subject to any disclaimer, the term of this patent is extended or adjusted under 35 U.S.C. 154(b) by 0 days.

(21) Appl. No.: 09/169,393

(22) Filed: Oct. 9, 1998

(51) Int. Cl.$^7$ .......................... A61B 17/20; A61M 1/00; A61H 1/00; A61H 5/00
(52) U.S. Cl. .......................... 604/22; 604/35; 604/542; 604/902; 601/2
(58) Field of Search .......................... 604/19–22, 27, 604/35, 73, 313–14, 264, 523, 538, 540, 542, 902, 500; 606/169–171, 32, 41, 167, 190; 601/2, 6; 210/406, 416.1

(56) References Cited

U.S. PATENT DOCUMENTS

| | | | | |
|---|---|---|---|---|
| 4,562,838 A | * | 1/1986 | Walker | 604/42 |
| 4,878,900 A | * | 11/1989 | Sundt | 604/119 |
| 4,886,491 A | * | 12/1989 | Parisi | |
| 5,236,414 A | | 8/1993 | Takasu | |
| 5,244,458 A | | 9/1993 | Takasu | |
| 5,419,761 A | | 5/1995 | Narayanan | |
| 5,458,631 A | * | 10/1995 | Zavier | 604/21 |
| 5,514,086 A | * | 5/1996 | Parisi | 604/22 |
| 5,527,273 A | * | 6/1996 | Manna | 604/22 |
| 5,620,447 A | * | 4/1997 | Smith et al. | 604/22 |
| 5,725,546 A | * | 3/1998 | Samson | 606/191 |
| 5,911,700 A | * | 6/1999 | Mozsary et al. | 604/22 |
| 6,117,150 A | * | 9/2000 | Pingleton et al. | |

OTHER PUBLICATIONS

Rod Rohrich, Separating Ultrasound–Assisted Lipoplasty Fact from Fiction Ultrasound–Assisted Lipoplasty Resource Guide, Plastic Surgery News, pp. 22–23, 1997.

*Ultrasound–Assisted Lipoplasy Resource Guide* PlasticSurgery News. The American society of Plastic and Reconstructive Surgeons.

* cited by examiner

*Primary Examiner*—Angela D. Sykes
*Assistant Examiner*—Patricia Bianco
(74) *Attorney, Agent, or Firm*—Merchant & Gould P.C.; Thomas H. Young

(57) ABSTRACT

In general the ultrasonic probe for improved fragmentation is comprised of a longitudinal shank having a proximal end, a distal end, and a shaft. The shaft joins the proximal end and the distal end. The proximal end of the longitudinal shank has a connector for connecting the longitudinal shank to a source of ultrasonic vibrational energy. The distal end of the longitudinal shank may have a blunt or bullet-nosed tip. The shaft has one or more grooves near the tip which circumscribe the shaft of the longitudinal shank.

The walls of the one or more grooves in the shaft of the longitudinal shank provide surface area on the distal end of the ultrasonic probe in planes generally perpendicular to the axis of the ultrasonic probe. The additional surface area increases the tissue fragmenting surface area of the distal end of the ultrasonic probe without increasing the diameter of the distal end of the ultrasonic probe. Thus, one is able to more rapidly and thoroughly fragment or emulsify tissues with a given diameter of the distal end of the ultrasonic probe. Further, because tissue typically does not contact the bottom of the grooves, the tissue contact surface area along and about the distal end of the ultrasonic probe is reduced, thus reducing the potential for tissue burns.

16 Claims, 4 Drawing Sheets

ULTRASONIC PROBE AND METHOD FOR IMPROVED FRAGMENTATION

CROSS-REFERENCE TO RELATED APPLICATION

Not Applicable

STATEMENT REGARDING FEDERALLY SPONSORED RESEARCH

Not Applicable

REFERENCE TO A MICROFICHE APPENDIX

Not Applicable

BACKGROUND OF THE INVENTION

This invention relates generally to surgical instruments, and, more particularly, to a surgical device for ultrasonic fragmentation or emulsification of soft tissues of a patient.

Liposuction is a surgical procedure for altering the human form, specifically by removal of localized deposits of fat tissues that are unresponsive to diet or exercise. The procedure is also known as suction lipectomy, lipolysis, and more recently as body contour surgery, body sculpting surgery, or suction-assisted liposuction. It is most often performed by plastic surgeons, although dermatologists, gynecologists, and other surgical specialties also perform the procedure.

The liposuction procedure is typically accomplished by inserting a small liposuction cannula through an incision in the skin, applying a suction source to the end of the liposuction cannula that remains outside of the body, and forcing the working end of the liposuction cannula forward and backward in the layer of fatty tissue. The fatty tissue is torn, crushed, or avulsed, and is then aspirated through small openings along the sides of the liposuction cannula near the tip and then through a central lumen in the liposuction cannula to a tissue canister placed in-line with the liposuction cannula and the suction source. The procedure may involve multiple incisions and many passes of the liposuction cannula in each incision to achieve the desired cosmetic effect for the patient.

A liposuction cannula is typically a small metal tube with a blunt, closed end at the tip of the liposuction cannula. The blunt, closed end at the tip of the liposuction cannula is intended to minimize damage to tissues as the device is thrust forward. Small openings along the sides of the liposuction cannula near the tip create passages between the tissue and the central lumen of the liposuction cannula, which is in fluid communication with a suction source, so that tissue and fluids can be aspirated. In general, the suction causes the adipose tissue to be sucked into the openings along the sides of the liposuction cannula, and the blunt dissection as provided by the surgeon's manipulation of the liposuction cannula, then tears the tissue. The fragments and released fluids are then aspirated through the openings along the sides of the liposuction cannula and then through the central lumen of the liposuction cannula.

The liposuction procedure can be traumatic for the patient. The liposuction cannula does not discriminate between adipose tissue and other tissues such as nerves, blood vessels, or lymph tissues. The mechanical disruption of the above-named tissues by the liposuction cannula may result in, among other things, bleeding, bruising, temporary numbness, or swelling. Further, the final cosmetic result achieved for the patient is a function of the skill of the surgeon, the patient, and the type of surgical instrumentation used in the surgery. Liposuction cannulae used in the liposuction procedure may remove more adipose tissue from one area than another area in the patient, resulting in skin contour irregularities and a final cosmetic result for the patient that is not smooth or uniform.

Therefore, there is a need to improve the design of liposuction cannulae to help the surgeon to better discriminate between adipose tissue and other tissues such as nerves, blood vessels, and lymph tissues, so that the adipose tissues can be fragmented and removed while the remaining tissues are damaged as little as possible or not at all. Further, there is a need to improve the design of current liposuction cannulae such that adipose tissue is removed in a uniform and predictable manner such that an improved cosmetic result is achieved for the patient.

Recently, several instruments have combined ultrasonic vibrations and the liposuction cannula to improve upon the tissue discrimination capability of the liposuction cannula and to provide an instrument, which removes adipose tissue more uniformly than current liposuction cannulae. This procedure is commonly referred to as ultrasound-assisted lipoplasty. In a typical ultrasound-assisted lipoplasty procedure, an ultrasonically vibrating cannula is inserted through an incision in the patient's skin and passed forward and backward through the adipose tissue layer. The ultrasonically vibrating cannula fragments or emulsifies the adipose tissues, which are then typically aspirated through a central lumen in the ultrasonically vibrating cannula.

Initial experiences with the ultrasound-assisted lipoplasty procedure have been mixed. A comparison of the suction-assisted liposuction and ultrasound-assisted lipoplasty approaches with currently available surgical instruments for both procedures was recently given in *Ultrasound-Assisted Lipoplasty Resource Guide*, published in PlasticSugery News, a publication of The American Society of Plastic and Reconstructive Surgeons, 1997. In the article the author cites the disadvantages of the current ultrasound-assisted lipoplasty procedure compared to the suction-assisted liposuction procedure as: 1) burns of the skin are possible, 2) longer incisions are needed, 3) seromas are more common, 4) longer operating times are required, and 5) greater expenses are incurred. Thus, current ultrasound-assisted lipoplasty surgical systems for fragmentation and aspiration of adipose tissues are more costly and slower than the suction-assisted liposuction procedure and have the potential to damage tissues beyond that of suction-assisted liposuction, including burns of the skin and seroma formation. There is, therefore, a need to reduce equipment expense, to increase the speed of the ultrasound-assisted lipoplasty procedure, and to minimize the potential for burns or seroma formation.

An ultrasonic probe for soft tissue fragmentation may be hollow, in which case the instrument may be referred to as an ultrasonic cannula, or it may be solid. The distal end of an ultrasonic probe experiences small, rapid excursions along an axis, which passes through proximal end and the distal end of the ultrasonic probe. A maximum distal end excursion of 350 µm peak-to-peak at 23 kHz has been obtained in a commercially available ultrasonic aspirator for neurosurgery, e.g., the CUSA of Valleylab Inc., Boulder, Colo. The small, rapid motions at the distal end of the ultrasonic probe fragment or emulsify soft tissues of the body, having the strongest effect upon tissues which come into direct contact with the frontal area of the distal end of the ultrasonic probe, in line with the long axis of the ultrasonic probe. These tissues experience powerful ultrasonic-frequency forces that may rupture cell membranes or dislodge entire cells or groups of cell from their attachments to the tissue bed. Tissues may also contact the surface area along and about the sides of the distal end of the ultrasonic probe. Rather than fragment, tissues that contact the sides of the distal end of the ultrasonic probe tend to heat and desiccate because the nature of the contact is a rapid rubbing motion as opposed to the powerful smashing motion at the frontal area of the distal end of the ultrasonic probe. Therefore, for effective and expedient soft tissue fragmentation and emulsification it is beneficial to maximize the frontal surface area at the distal end of the ultrasonic probe in that plane generally perpendicular to the long axis of the ultrasonic probe. To minimize the potential for tissue burns it is likewise beneficial to minimize the tissue contact area along and about the sides of the distal end of the ultrasonic probe. The frontal area of the distal end of the ultrasonic probe has a maximum value, which is a function of the diameter of the distal end of the ultrasonic probe. The diameter of the ultrasonic probe may be increased to increase the frontal area of the distal end of the ultrasonic probe but this requires larger incisions in the patient to accommodate the larger diameter ultrasonic probe.

Further, if a lumen is present, in the center of the ultrasonic probe and aligned with the long axis of the ultrasonic probe, the frontal area of the distal end of the ultrasonic probe, in a plane generally perpendicular to the long axis of the ultrasonic probe, is further reduced by the cross-sectional area of the lumen. Therefore, there is a need to improve the design of the distal end of ultrasonic probes so that the surface area in planes generally perpendicular to the long axis of the ultrasonic probe is increased without increasing the diameter of the ultrasonic probe. Further, there is a need to improve the design of the distal end of ultrasonic probes so that the tissue contact area along and about the sides of the distal end of the ultrasonic probe is reduced.

Many patents disclose improvements and solutions for ultrasound-assisted lipoplasty instruments for removal of adipose tissue from the human body. U.S. Pat. No. 4,886,491 to Parisi has a method of removing fatty tissue from a patient using an ultrasonic probe and its energy application to melt at least some of the fatty tissue. U.S. Pat. No. 5,244,458 to Takasu has an ultrasonic handpiece with a hollow cannula with a plurality of suction openings in that cannula. U.S. Pat. No. 5,236,414 also to Takasu has an ultrasonic handpiece with a tip having a tubular body and a suction passage. U.S. Pat. No. 5,419,761 to Narayanan has an ultrasonic handpiece with a rigid tube with an axially extending lumen. U.S. Pat. No. 5,514,086 to Parisi has an ultrasonic handpiece with a probe and a tip on the probe. The tip has an acoustic impedance substantially greater than that of the probe. U.S. Pat. No. 5,527,273 to Manna has an ultrasonic lipectomy probe with an enlarged head on the distal end and a longitudinally extending channel in the probe.

While some of the patented devices may disclose and claim improvements and solutions to ultrasound-assisted lipoplasty instruments, none address or appreciate the needs and design considerations discussed above for effective and expedient soft tissue fragmentation or emulsification using an ultrasonic probe. Further, none of the above-named patents address or appreciate the tissue heating and desiccation problems caused by the rubbing motion between the sides of distal end of the ultrasonic probe and the tissue.

OBJECTS OF THE INVENTION

It is, among other desirable attributes, a general object of the present invention to provide an improved ultrasonic probe for fragmentation or emulsification of soft tissues in a patient.

It is a further object of the present invention to provide an improved ultrasonic probe for fragmentation or emulsification of soft tissues in a patient which maximizes the fragmentation or emulsification of adipose tissues and minimizes trauma to all other contacted tissues such as nerves, blood vessels, and lymph tissues, and thus decreases healing time, decreases patient pain, reduces swelling, and decreases bleeding.

It is still a further object of the present invention to provide an improved ultrasonic probe for fragmentation or emulsification of soft tissues in the patient that increases the speed of the fragmentation or emulsification process and thereby reduces the time required to complete the surgical procedure.

It is a yet still a further object of the present invention to provide an improved ultrasonic probe for fragmentation or emulsification of soft tissues in a patient which provides uniform, controllable, and predictable fragmentation or emulsification of soft tissues and which therefore yields an improved cosmetic result for the patient.

It is a specific object of the present invention to maximize the tissue fragmenting surface area of the distal end of the ultrasonic probe in planes generally perpendicular to the long axis of the ultrasonic probe.

It is a further specific object of the present invention to minimize the tissue contact surface area along and about the sides of the distal end of the ultrasonic probe.

SUMMARY OF THE INVENTION

In general the ultrasonic probe for improved fragmentation is comprised of a longitudinal shank having a proximal end and a distal end. A shaft of the longitudinal shank joins the proximal end and the distal end. An axis of the longitudinal shank is aligned with the center of the longitudinal shank and passes through the proximal end and the distal end. The preferred shape for cross-sections of the longitudinal shank perpendicular to the axis of the longitudinal shank is round. The preferred material for the longitudinal shank is titanium or a titanium alloy such as Ti6Al4V. The proximal end of the longitudinal shank has a connection for connecting the longitudinal shank to a source of ultrasonic vibrational energy. The preferred means for connecting the longitudinal shank to the source of ultrasonic vibrational energy is a threaded stud which mates with a female threaded hole in the proximal end of the longitudinal shank and another female threaded hole in the source of ultrasonic vibrational energy. The distal end of the longitudinal shank has a tip. The preferred shape for the tip is blunt or bullet-nosed with smooth and rounded edges about and around the circumference where the tip is attached to the distal end of the longitudinal shank. The shaft of the longitudinal shank has one or more grooves near the tip, the grooves which substantially circumscribe the shaft and that are generally transverse to the axis of the longitudinal shank.

The walls of the one or more grooves in shaft of the longitudinal shank provide surface area on the distal end of the longitudinal shank in planes generally perpendicular to the axis of the longitudinal shank. The additional surface area increases the tissue fragmenting surface area of the distal end of the longitudinal shank without increasing the diameter of the distal end of the longitudinal shank. Thus, one is able to more rapidly and thoroughly fragment or emulsify adipose tissues with a given diameter of the distal end of the longitudinal shank. Further, because tissue typically does not contact the bottoms of the one or more grooves, the tissue contact surface area along and about the distal end of the longitudinal shank is reduced, thus reducing the potential for tissue burns.

The one or more grooves in the shaft of the longitudinal shank near the tip may be of any shape. The preferred shape is a square-bottomed groove, such that the bottom of any groove, in a cross-section that contains the axis, is substantially flat and substantially parallel to the axis of the longitudinal shank, and the walls and the bottom of any groove form approximately right angles. Other possible shapes include a V-bottomed groove and a U-bottomed groove.

In a further refinement of the ultrasonic probe the one or more grooves in the shaft of the longitudinal shank may not completely circumscribe the shaft of the longitudinal shank.

In a still further refinement of the ultrasonic probe the longitudinal shank may be solid or the longitudinal shank may be hollow, having an open lumen along its length, aligned with the axis of the longitudinal shank, and located generally in the center of the longitudinal shank.

In yet a still further refinement of the ultrasonic probe the longitudinal shank may have a tapered section, the tapered section positioned along the axis of the longitudinal shank and between the shaft of the longitudinal shank and the distal end of the longitudinal shank. The tapered section has a generally decreasing diameter from the shaft of the longitudinal shank to the distal end of the longitudinal shank.

A second embodiment of the ultrasonic probe for improved fragmentation is comprised of a longitudinal shank having a proximal end and a distal end. A shaft of the longitudinal shank joins the proximal end and the distal end. An axis of the longitudinal shank is aligned with the center of the longitudinal shank and passes through the proximal end and the distal end. The preferred shape for cross-sections of the longitudinal shank perpendicular to the axis of the longitudinal shank is round. The preferred material for the longitudinal shank is titanium or a titanium alloy such as Ti6Al4V. The proximal end of the longitudinal shank has a connection for connecting the longitudinal shank to a source of ultrasonic vibrational energy. The preferred means for connecting the longitudinal shank to the source of ultrasonic vibrational energy is a threaded stud which mates with a female threaded hole in the proximal end of the longitudinal shank and another female threaded hole in the source of ultrasonic vibrational energy. The distal end of the longitudinal shank has a tip. The preferred shape for the tip is blunt or bullet-nosed with smooth and rounded edges about and around the circumference where the tip is attached to the distal end of the longitudinal shank. In the second embodiment one or more flanges may protrude radially and outwardly from the shaft near the tip. The flanges may substantially circumscribe the shaft near the tip and are substantially perpendicular to the axis of the longitudinal shank.

In a further refinement of the ultrasonic probe the one or more flanges do not completely circumscribe the shaft of the longitudinal shank.

In a still further refinement of the ultrasonic probe the longitudinal shank may be solid or the longitudinal shank may be hollow, having an open lumen along its length, aligned with the axis of the longitudinal shank, and located generally in the center of the longitudinal shank.

In yet a still further refinement of the ultrasonic probe the longitudinal shank may have a tapered section, the tapered section positioned along the axis of the longitudinal shank and between the shaft of the longitudinal shank and the distal end of the longitudinal shank. The tapered section has a generally decreasing diameter from the shaft of the longitudinal shank to the distal end of the longitudinal shank.

Also claimed is a method of using an ultrasonic probe for fragmenting or emulsifying a medium with axially applied ultrasonic vibrations which includes the steps of: vibrating an elongate probe along an axis between proximal and distal ends thereof at ultrasonic frequencies, engaging the medium with the distal end of the elongate probe, the distal end of the elongate probe with a tip and one or more grooves or flanges which substantially circumscribe a shaft of the elongate probe near the distal end, and fragmenting or emulsifying the medium with the distal end of the elongate probe:

BRIEF DESCRIPTION OF THE DRAWINGS

The novel features of the invention are set forth in the appended claims. The invention will be best understood by reference to the following figures when read in conjunction with the detailed description of the invention.

DETAILED DESCRIPTION OF THE INVENTION

Figure 1:
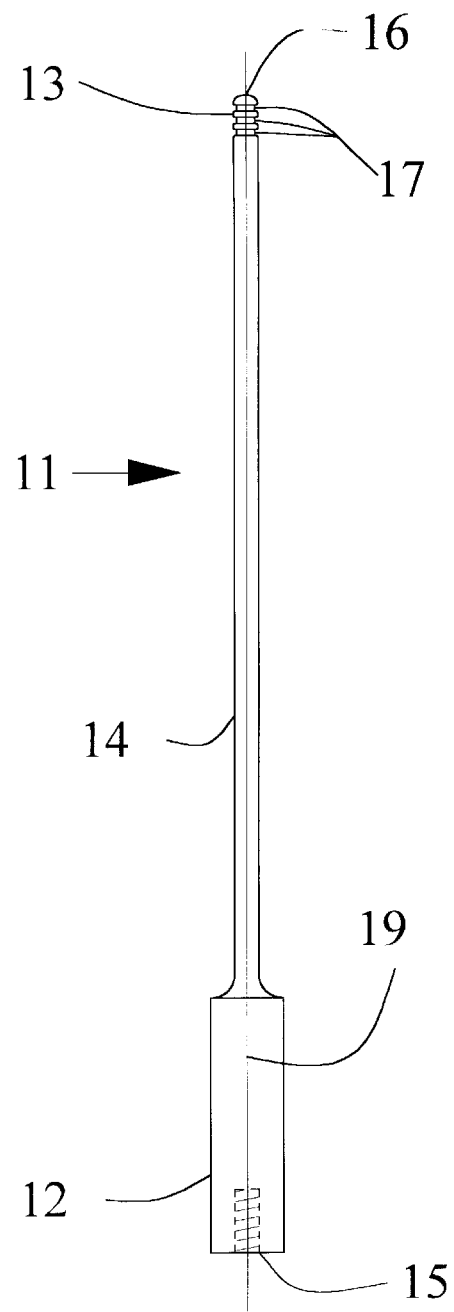
FIG. 1 is a side view of the ultrasonic probe with a straight shaft.

Referring to the drawings, FIG. 1 illustrates a side view of an ultrasonic probe embodying this invention. The ultrasonic probe includes a longitudinal shank 11, the shank comprised of a proximal end 12, a distal end 13, and a shaft 14. The shaft 14 joins the proximal end 12 and the distal end 13. An axis 19, illustrated with a phantom line, of the longitudinal shank 11 is aligned with the center of the longitudinal shank 11 and passes through the proximal end 12 and the distal end 13. The preferred shape for cross-sections of the longitudinal shank 11 perpendicular to the axis 19 of the longitudinal shank 11 is round. The preferred material for the longitudinal shank 11 is titanium or a titanium alloy such as Ti6Al4V. The proximal end 12 has a connection 15 for connecting the longitudinal shank 11 to a source of vibrational energy. The preferred means for connecting the longitudinal shank 11 to the source of ultrasonic vibrational energy is a threaded stud which mates with a female threaded hole in the proximal end 12 of the longitudinal shank 11 and a second female threaded hole in the source of ultrasonic vibrational energy. The longitudinal shank 11 has a tip 16 on the distal end 13. The preferred shape for the tip 16 is blunt or bullet-nosed with smooth and rounded edges about and around the circumference where the tip 16 is attached to the distal end 13. The shaft 14 may have one or more grooves 17 near the tip 16. The grooves 17 substantially circumscribe the shaft 14 of the longitudinal shank 11 and are generally transverse to the axis 19 of the longitudinal shank 11.

Figure 2:
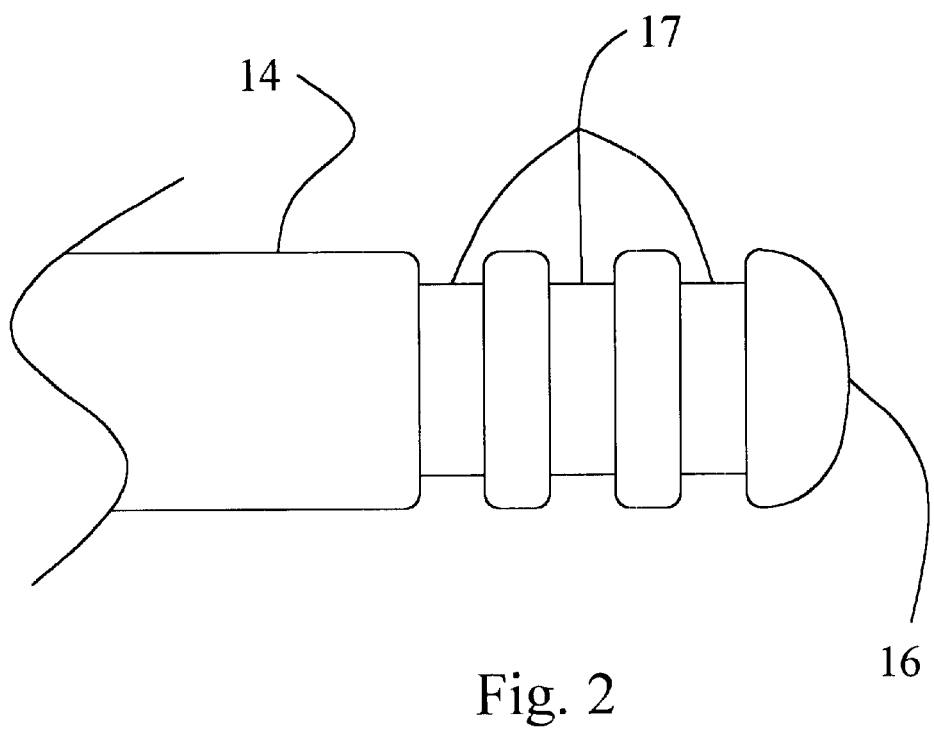
FIG. 2 is a detailed side view of the distal end of the ultrasonic probe, showing grooves with bottoms substantially flat and substantially parallel to the axis of the longitudinal shank.

A detailed side view of the distal end 13 of the longitudinal shank 11 is shown in FIG. 2. The shaft 14 may have one or more grooves 17 near the tip 16 which substantially circumscribe the shaft 14. Three grooves 17 are shown. The grooves 17 have bottoms which are substantially flat and substantially parallel to the axis 19 of the longitudinal shank 11, as apparent in the side-view of FIG. 2. While the cross-sectional shapes of the grooves 17 may vary in the Figures herein, the reference numbers for similar elements will, for simplicity, be the same throughout this disclosure.

Figure 3:
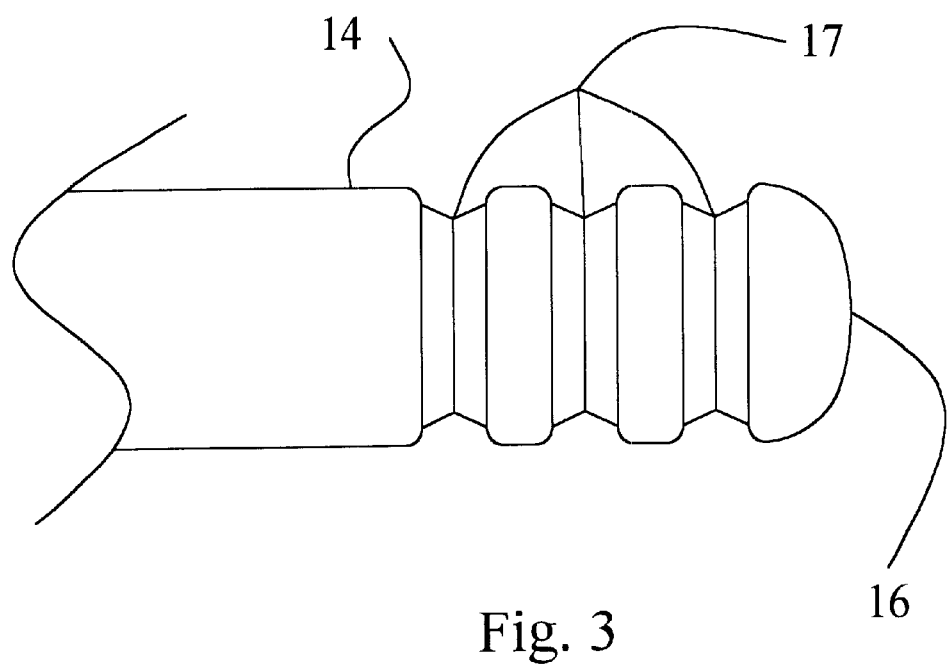
FIG. 3 is a detailed side view of the distal end of the ultrasonic probe, showing V-bottomed grooves.

Another detailed side view of the distal end 13 of the longitudinal shank 11 is shown in FIG. 3. The shaft 14 may have one or more grooves 17 near the tip 16 which substantially circumscribe the shaft 14. Three grooves 17 are shown. The grooves 17 are V-bottomed grooves as apparent in the side-view of FIG. 3.

Figure 4:
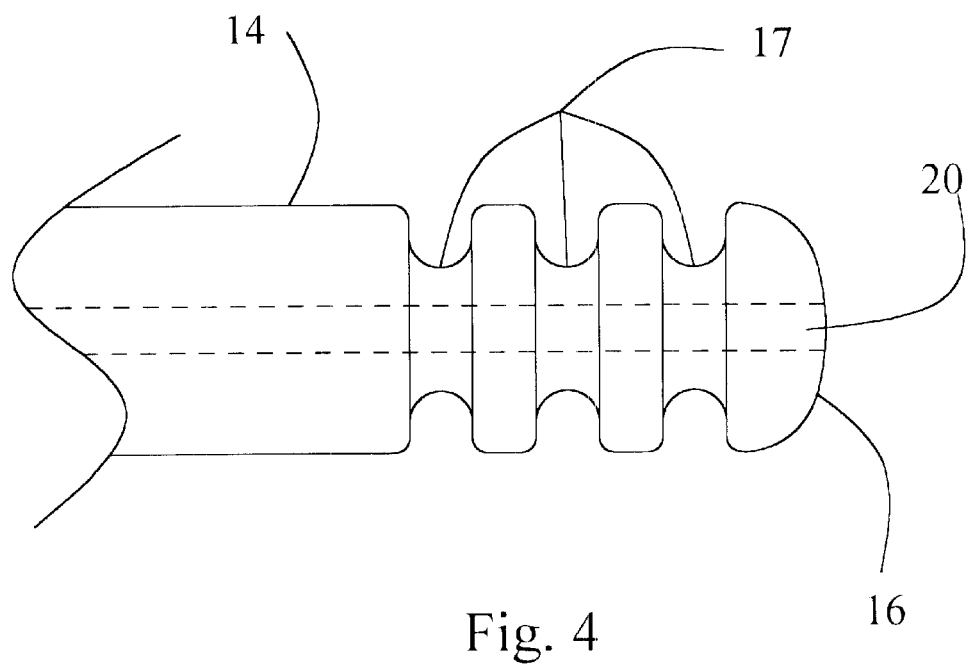
FIG. 4 is a detailed side view of the distal end of the ultrasonic probe, showing U-bottomed grooves and an open lumen in the longitudinal shank.

Still another detailed side view of the distal end 13 of the longitudinal shank 11 is shown in FIG. 4. The shaft 14 may have one or more grooves 17 near the tip 16 which substantially circumscribe the shaft 14. Three grooves 17 are shown. The grooves 17 are U-bottomed grooves as apparent in the side-view of FIG. 4. FIG. 4 also shows an open lumen 20, aligned with the axis of the longitudinal shank 11 and located generally in the center of the longitudinal shank 11. The open lumen 20 extends for the full length of the longitudinal shank 11, but is only shown in the distal end 13 in FIG. 4.

Figure 5:
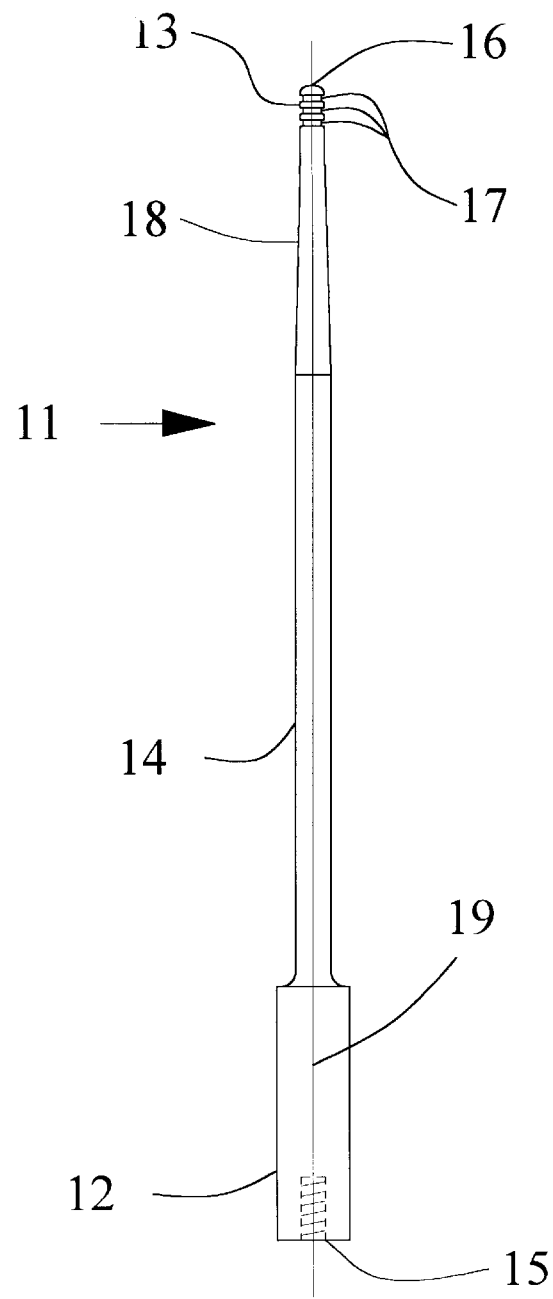
FIG. 5 is a side view of the ultrasonic probe with a tapered section in the longitudinal shank.

A side view of a refinement to or alternate of the longitudinal shank 11 is shown in FIG. 5. In this refinement the ultrasonic probe includes a longitudinal shank 11, the shank comprised of a proximal end 12, a distal end 13, and a shaft 14. The longitudinal shank 11 has a shaft 14 that includes a tapered section 18, the tapered section 18 positioned along the axis 19 of the longitudinal shank 11 and between the shaft 14 which is untapered and the distal end 13 of the longitudinal shank 11. The tapered section 18 has a diameter that generally decreases from the shaft 14 to the distal end 13 or the longitudinal shank 11. The proximal end 12 has a connection 15 for connecting the longitudinal shank 11 to a source of vibrational energy. The longitudinal shank 11 has a tip 16 on the distal end 13. The preferred shape for the tip 16 is blunt or bullet-nosed with smooth and rounded edges about and around the circumference where the tip 16 is attached to the distal end 13. The tapered section 18 may also have one or more grooves 17 near the tip 16, but that is not shown. The grooves 17 would thus substantially circumscribe the tapered section 18 of the longitudinal shank 11.

Figure 6:
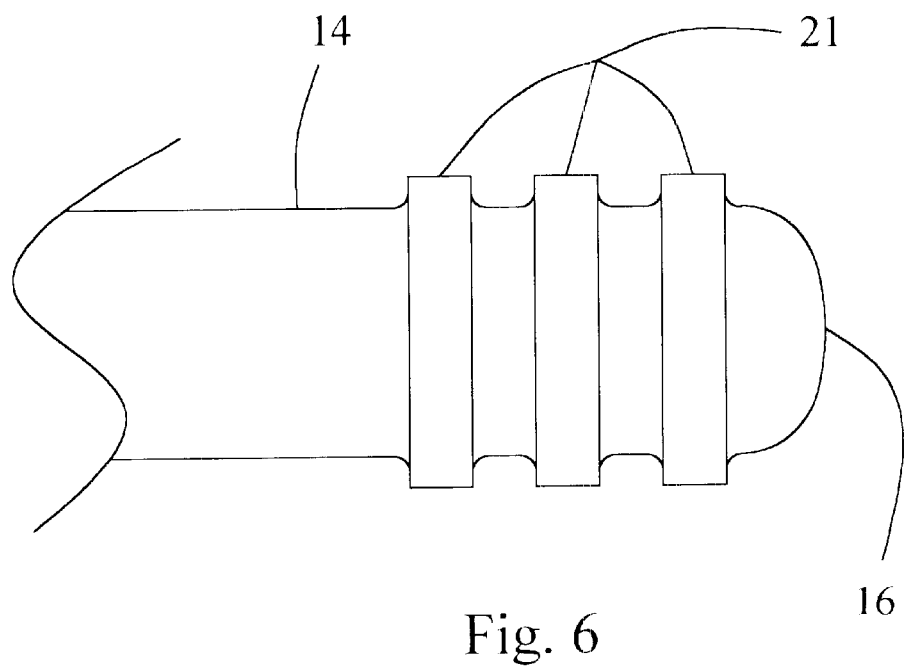
FIG. 6 is a detailed side view of the distal end of the ultrasonic probe, showing flanges.

A detailed side view of the distal end 13 of the longitudinal shank 11 with flanges 21 is shown in FIG. 6. The one or more flanges 21 protrude radially and outwardly from the shaft 14 near the tip 16. Three flanges 21 are shown.

Figure 7:
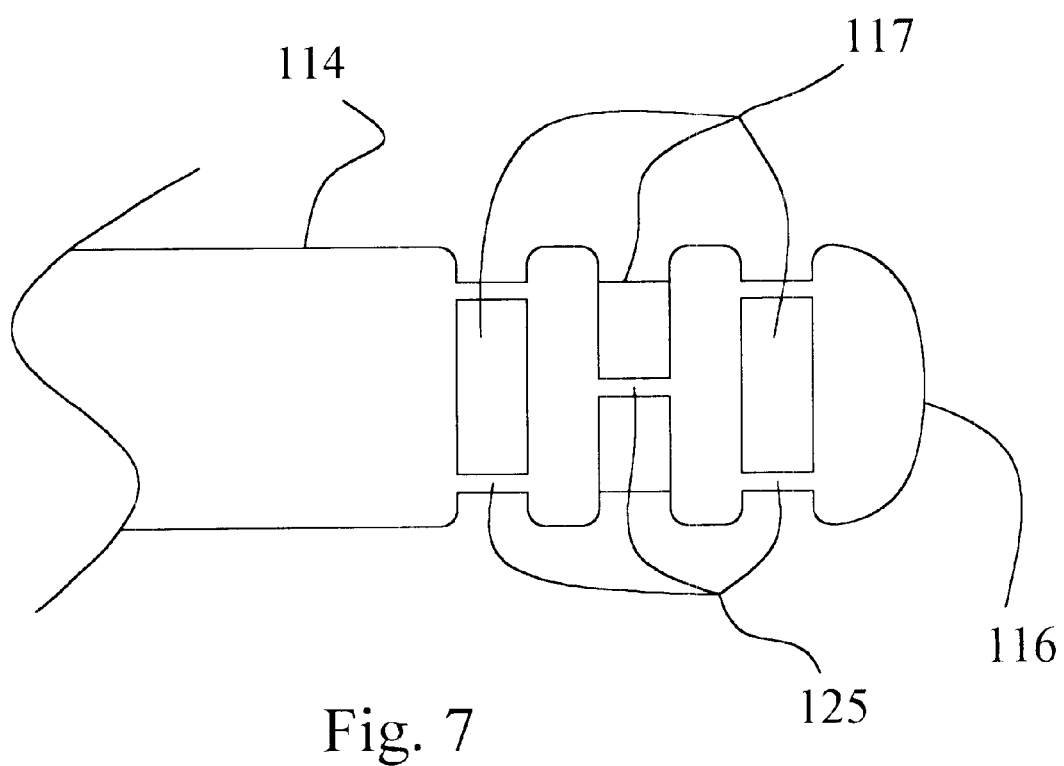
FIG. 7 depicts one embodiments of the invention in which the grooves extend substantially, but not completely, around the shaft of the ultrasonic prode.

FIG. 7 illustrates one form of the present invention previously described in which the grooves 117 substantially, but not completely, circumscribe the shank 114 near the tip 116. In this case each groove is interrupted by three ridges 125.

While particular designs are disclosed and described the ultrasonic probes for which protection is sought are those that offer greater surface area in planes generally perpendicular to the axis of the longitudinal shank for improved tissue fragmentation and reduced contact surface area on the sides of the distal end of the ultrasonic probe for reduced heat generation in the tissue. The claims which follow seek to cover that apparatus and method. Although not shown, various alterations may be used by skilled artisans. For instance, while grooves are shown and described, a threaded or cross-threaded distal end could suffice.

What is claimed is:

1. An ultrasonic probe for fragmenting or emulsifying soft tissues in a patient, the ultrasonic probe powered by a source of ultrasonic vibrational energy, the ultrasonic probe comprising:

a longitudinal shank having a proximal end and a distal end;

a shaft of the longitudinal shank joining the proximal end and the distal end;

an axis of the longitudinal shank aligned with the center of the longitudinal shank and passing through the proximal end and the distal end;

a connection at the proximal end of the longitudinal shank for connecting the longitudinal shank to the source of ultrasonic vibrational energy;

a tip at the distal end of the longitudinal shank; and one or more grooves near the tip, the grooves being generally transverse to the axis, in the shaft of the longitudinal shank, and substantially circumscribing the shaft of the longitudinal shank thereby reducing the tissue contact surface area along and about the sides of the tip and providing additional tissue fragmenting surface area of the tip in planes generally perpendicular to the axis.

2. The ultrasonic probe of claim 1 wherein the one or more grooves each have a bottom, each bottom, in a cross-section containing the axis of the longitudinal shank, that is substantially flat and substantially parallel to the axis of the longitudinal shank.

3. The ultrasonic probe of claim 2 wherein each bottom of the one or more grooves has a U-shape in a cross-section containing the axis of the longitudinal shank.

4. The ultrasonic probe of claim 1 wherein the one or more grooves do not completely circumscribe the shaft.

5. The ultrasonic probe of claim 1 wherein the longitudinal shank is solid.

6. The ultrasonic probe of claim 1 wherein the longitudinal shank is hollow having an open lumen along its length, aligned with the axis of the longitudinal shank, and located generally in the center of the longitudinal shank.

7. The ultrasonic probe of claim 1 wherein the longitudinal shank has a tapered section, the tapered section positioned along the axis of the longitudinal shank and between the shaft of the longitudinal shank and the distal end of the longitudinal shank, the tapered section such that the diameter generally decreases from the shaft of the longitudinal shank to the distal end of the longitudinal shank.

8. The ultrasonic probe of claim 1 wherein the tip at the distal end of the longitudinal shank has a blunt or bullet-nosed shape.

9. An ultrasonic probe for fragmenting or emulsifying soft tissues in a patient, the ultrasonic probe powered by a source of ultrasonic vibrational energy, the ultrasonic probe comprising:

a longitudinal shank having a proximal end and a distal end;

a shaft of the longitudinal shank joining the proximal end and the distal end;

an axis of the longitudinal shank aligned with the center of the longitudinal shank and passing through the proximal end and the distal end;

a connection at the proximal end of the longitudinal shank for connecting the longitudinal shank to the source of ultrasonic vibrational energy;

a tip at the distal end of the longitudinal shank; and one or more flanges protruding radially and outwardly from the shaft near the tip, the flanges substantially circumscribing the shaft of the longitudinal shank and being substantially perpendicular to the axis of the longitudinal shank thereby reducing the tissue contact surface area along and about the sides of the tip and providing additional tissue fragmenting surface area of the tip in planes generally perpendicular to the axis.

10. The ultrasonic probe of claim 9 wherein the one or more flanges do not completely circumscribe the shaft.

11. The ultrasonic probe of claim 9 wherein the longitudinal shank is solid.

12. The ultrasonic probe of claim 9 wherein the longitudinal shank is hollow having an open lumen along its length, aligned with the axis of the longitudinal shank, and located generally in the center of the longitudinal shank.

13. The ultrasonic probe of claim 9 wherein the longitudinal shank has a tapered section, the tapered section positioned along the axis of the longitudinal shank and between the shaft of the longitudinal shank and the distal end of the longitudinal shank, the tapered section such that the diameter generally decreases from the shaft of the longitudinal shank to the distal end of the longitudinal shank.

14. The ultrasonic probe of claim 9 wherein the tip at the distal end of the longitudinal shank has a blunt or bullet-nosed shape.

15. An ultrasonic probe for fragmenting or emulsifying soft tissues in a patient, the ultrasonic probe powered by a source of ultrasonic vibrational energy, the ultrasonic probe comprising:

a longitudinal shank having a proximal end and a distal end;

a shaft of the longitudinal shank joining the proximal end and the distal end;

an axis of the longitudinal shank aligned with the center of the longitudinal shank and passing through the proximal end and the distal end;

a connection at the proximal end of the longitudinal shank for connecting the longitudinal shank to the source of ultrasonic vibrational energy;

a tip at the distal end of the longitudinal shank;

one or more grooves near the tip, the grooves being generally transverse to the axis, in the shaft of the longitudinal shank, and substantially circumscribing the shaft of the longitudinal shank thereby reducing the tissue contact surface area along and about the sides of the tip and providing additional tissue fragmenting surface area of the tip in planes generally perpendicular to the axis;

said grooves each having a bottom with a V-shape in a cross-section containing the axis of the longitudinal shank.

16. A method of fragmenting or emulsifying soft tissue in a patient with axially applied ultrasonic vibrations, the method comprising:

vibrating an elongate probe along an axis between proximal and distal ends thereof at ultrasonic frequencies;

engaging the soft tissue with the distal end of the elongate probe, the distal end of the elongate probe with a tip and one or more grooves or flanges near the tip, said grooves or flanges being substantially perpendicular to the axis and substantially circumscribing a shaft of the elongate probe near the tip, thereby reducing the tissue contact surface area along and about the sides of the tip and providing additional tissue fragmenting surface area of the tip in planes generally perpendicular to the axis; and fragmenting or emulsifying the soft tissue with the distal end of the elongate probe.

* * * * *